US007412395B2

(12) United States Patent
Rowlandson

(10) Patent No.: US 7,412,395 B2
(45) Date of Patent: Aug. 12, 2008

(54) AUTOMATED SCHEDULING OF EMERGENCY PROCEDURE BASED ON IDENTIFICATION OF HIGH-RISK PATIENT

(75) Inventor: G. Ian Rowlandson, Milwaukee, WI (US)

(73) Assignee: GE Medical Systems Information Technologies, Inc., Milwaukee, WI (US)

( * ) Notice: Subject to any disclaimer, the term of this patent is extended or adjusted under 35 U.S.C. 154(b) by 1574 days.

(21) Appl. No.: 09/751,023

(22) Filed: Dec. 29, 2000

(65) Prior Publication Data

US 2002/0087355 A1 Jul. 4, 2002

(51) Int. Cl.
*G06Q 50/00* (2006.01)
(52) U.S. Cl. .............................. 705/2; 600/508; 600/509
(58) Field of Classification Search .................. 705/2, 705/3; 600/300, 508, 509; 514/12; 434/262
See application file for complete search history.

(56) References Cited

U.S. PATENT DOCUMENTS

| 3,724,455 A | * | 4/1973 | Unger ......................... 600/515 |
| 5,339,821 A | * | 8/1994 | Fujimoto ..................... 600/513 |
| 5,517,405 A | * | 5/1996 | McAndrew et al. ........... 706/45 |
| 5,544,661 A | | 8/1996 | Davis et al. .................. 128/700 |
| 6,004,266 A | * | 12/1999 | Clawson ...................... 600/300 |
| 6,345,260 B1 | * | 2/2002 | Cummings et al. ............. 705/8 |
| 2002/0107206 A1 | * | 8/2002 | Coolidge et al. .............. 514/21 |
| 2005/0060198 A1 | * | 3/2005 | Bayne ........................... 705/2 |

FOREIGN PATENT DOCUMENTS

WO WO 99/55227 11/1999
WO WO 00/30529 6/2000

OTHER PUBLICATIONS

Sauer, J., Bruns, R. "Knowledge-based Scheduling System in Industry and Medicine." IEEE Expert. New York: Jan. 1997. vol. 12, Iss. 1; p. 24-31.*
Bharadwaj, A., Sen, A., Vinze, A. "Scheduling Cardiac Procedures: A Knowledge-based Approach." IEEE Transactions on Engineering Management. New Yourk: Aug. 1999. vol. 46, Iss. 3, p. 322-334.*
"Lifenet RS Receiving Station from Medtronic Physio-Control Can Help Improve Heart Attack Diagnosis and Treatment," Medtronic News Release, Online Oct. 7, 1999, XP002195316.

* cited by examiner

*Primary Examiner*—C Luke Gilligan
*Assistant Examiner*—Martin A Gottschalk
(74) *Attorney, Agent, or Firm*—Ostrager Chong Flaherty & Broitman P.C.

(57) ABSTRACT

A system and a method for scheduling an emergency procedure in response to detecting that a patient has a high probability of acute myocardial infarction. The system is able to identify patients that are suspected of having acute myocardial infarction (or acute ischemia). The system uses one or more expert software tools or algorithms to analyze received ECG records. Each software tool has logic (e.g., thresholds and/or settings) for automatic routing which is configurable by the customer via a graphical user interface. If any sufficient condition for automatic routing is satisfied, the system routes the data (including the underlying ECG record) and an alert to an electronic device which is accessible by the cardiologist "on call" via a bidirectional pager. If the cardiologist decides that the requested emergency treatment or procedure should be performed, the system accesses the schedules of all associated catheterization labs across multiple hospitals to identify a lab having optimum time-to-treatment. Then the system automatically contacts the selected catheterization lab via a network to schedule the PTCA procedure.

23 Claims, 8 Drawing Sheets

AUTOMATED SCHEDULING OF EMERGENCY PROCEDURE BASED ON IDENTIFICATION OF HIGH-RISK PATIENT

FIELD OF THE INVENTION

This invention relates to the acquisition, analysis and routing electrocardiograms (ECGs) and other physiological data. In particular, the invention relates to scheduling of prompt emergency treatment for high-risk patients identified via automated monitoring of acquired ECGs.

BACKGROUND OF THE INVENTION

In hospitals or other health-care settings, it is frequently necessary to observe critical physiological conditions of a patient, including cardiovascular conditions. Cardiovascular condition data is obtained from sensors applied to a patient, or by imaging and sensing devices. Further, cardiovascular data may be data reported by a cardiologist based on review of a patient or a patient's monitor or image data. Hospitals or health-care centers often have hundreds or even thousands of sensor and metering devices and hundreds or even thousands of cardiac patients that require monitoring periodically over a lifetime. This data may be stored in a database for archival functions and later retrieval.

A known ECG management system, the MUSE® (Marquette Universal System for Electrocardiography) system of GE Marquette Medical Systems, Inc., is a software-based product that runs on off-the-shelf hardware. In particular, this ECG management system comprises a database of ECGs plus applications software. The MUSE® system receives ECG data from a multiplicity of instruments via a plurality of networks, analyzes that ECG data using various programs such as a serial comparison program, generates reports containing the results of the analysis, and then routes those reports to various systems and peripheral devices. In particular, the MUSE® system has automatic report routing which can send reports to multiple devices, including a facsimile machine as well as a digital pager.

In the known system, each ECG received by the MUSE® system has been analyzed by the instrument which acquired the ECG. Each instrument incorporates ECG analysis programs such as 12SL® from GE Marquette Medical Systems, Inc., which is a computer program for analyzing simultaneously acquired 12-lead ECGs. The 12SL® program makes precise measurements of recorded cardiac signals, and then provides an interpretation of the ECG waveforms using ECG interpretation criteria for both rhythm and morphology. This generates diagnostic statements. The ECG information stored by MUSE® system contains waveforms, measurements and diagnostic statement. The serial comparison program uses all of these. It can also re-measure the waveforms and recalculate measurements and criteria. The serial comparison program can do this on both the current and previous ECG.

Another known expert software tool used in cardiology is the ACI-TIPI (Acute Cardiac Ischemia Time-Insensitive Predictive Instrument), which uses a logistic regression-based equation for computing the probability that the patient is experiencing ischemia.

The accuracy of any one of the foregoing expert software tools is directly dependent upon the quality of the signal it acquires. In 1979, Marquette introduced an electrocardiograph that simultaneously acquired all of the leads from the 12-lead electrocardiogram. Prior to this time, all commercially available electrocardiographs could only acquire 3 leads at a time. Simultaneous recording was adopted so that the computer could use all signals from all 12 leads to properly detect and classify each QRS complex. The program also applies digital filters which remove power line noise and baseline sway.

Computer measurement of features within the QRS complex is very susceptible to artifact. In addition to filtering, there is another method of eliminating noise from the QRS complex: signal averaging. Instead of analyzing a single QRS complex, the Marquette 12SL® program generates a median complex. That is, it aligns in time, all of the QRS complexes of the same shape; it then generates a representative complex from the median voltages that are found at each successive sample time. This is more complicated than an average, but the method results in a cleaner signal since it disregards outliers.

All ECG computer programs are composed of two parts: one which measures the waveforms, the other which does the interpretation based on these measurements. The main task of the measurement section is to find the location of the major reference points (that is, the onsets and offsets of the P, QRS and T complexes). Consistent with the signal processing portion of the 12SL® program, the onsets and offsets of the major waves are delineated by an analysis of the slopes in all 12 simultaneous leads. That is, QRS duration is measured from the earliest onset in any lead to the latest deflection in any lead. Similarly, the QT interval is measured from the earliest detection of depolarization in any lead to the latest detection of re-polarization in any lead.

After the onsets and offsets of the P, QRS, and T complexes have been demarcated, the waves within each complex are measured according to published standards. These amplitudes and durations result in a measurement matrix containing more than 1600 values. This is then passed to the criteria portion of the 12SL® program so that it can generate an interpretation, including diagnostic statements referenced via a statement library.

The MUSE® system stores ECGs in such a fashion that they can be re-analyzed by the 12SL® program or other expert software tool. That is, the fidelity of the stored ECG is such that it can be used as if it were freshly acquired from the patient.

Computerized electrocardiography has resulted in two practical advantages for the overreading physician. First, the computer serves as an additional expert opinion. Second, it is possible for cardiologists to overread computer-analyzed tracings in half the time required for conventional, non-analyzed ECGs. Therefore, the computer is not only used to efficiently record, store, transmit, and present the ECG—it is also used to assist the physician in overreading the ECG.

Marquette's serial comparison program helps reduce the number of unnecessary admissions to coronary care units (CCUs) by speeding the evaluation of "questionable" or "borderline" ECGs. The program, which runs on the MUSE® system, compares a patient's current ECG with previous ECGs. The technique of comparing the current ECG to the previous ECG of a patient is termed serial electrocardiography. Serial electrocardiography is used to identify changes in the patient's electrocardiogram. The Marquette serial comparison program was developed to use statements, ECG measurements and waveform comparison techniques to maximize performance and accuracy in the detection of clinically significant changes in rhythm, P, QRS, ST and T waves. The Marquette MUSED system, which stores ECGs with physician-edited interpretations to both individual ECGs and serial comparisons, in tandem with the serial comparison program, allows for accurate and expedient processing of a patient's ECG data. It completes the comparison within minutes, and returns the report while the patient is still in the emergency room. Serial comparison saves time and money by promptly providing diagnostically useful information that helps reduce unneeded CCU admissions.

Serial comparison can provide a quick evaluation of many difficult-to-interpret ECG features, including the borderline Q waves of possible myocardial infarction, the mild ST segment elevation of possible myocardial injury and moderate ST segment elevation with Q-wave evidence of myocardial infarction, which may be persistent change resulting from old infarction. The precise, computerized comparison helps the physician to determine whether the patient has experienced an infarction, whether it is old or new, or whether the ECG reflects a variation that is normal for that patient.

Serial comparison is extremely quick and easy to use. The ECG in question is transmitted from the acquiring electrocardiograph to the MUSE® system using an automatic request for serial comparison of the patient's current and past ECGs. (The MUSE® system automatically stores a patient's successive ECGs.) Within minutes, the physician receives a serial comparison report, including previous ECGs, so that the physician can make his/her own visual comparisons.

It is normal to have significant day-to-day variation in the ECG waveform, and an ECG management system must be able to discriminate between normal and clinically significant variations. Certain clinical conditions can only be reliably detected via a serial analysis. The serial comparison program can detect a new left bundle branch block (LBBB) in an ECG series. It does this based on the ECG interpretation as well as direct comparison of the waveforms.

Acute myocardial infarction (a heart attack) is the leading cause of death in the United States of America. Acute myocardial infarction is often detected through serial change. The pertinent clinical changes in the ECG waveform include a small change in the so-called ST segment and a small new Q wave. These changes in the ECG waveform are typical of the evolution of acute myocardial infarction and must be detected in the face of normal variation.

The 12SL® ECG analysis program (and the other expert software tools discussed above) is able to identify those patients who have a high probability of acute coronary syndrome, i.e., unstable angina/acute myocardial infarction. These patients are candidates for an emergency procedure known as percutaneous transluminal coronary angioplasty (PTCA), which is performed in a catheterization lab at a hospital or health care facility. Time-to-treatment is critical for this procedure. In-hospital patient mortality for primary PTCA has been shown to vary from 2% to 22%, a tenfold difference. Delay in getting the patient into the catheterization lab has been found to be the most important variable for reducing mortality and improving overall outcome. The time-to-treatment for the PTCA procedure often exceeds the recommended guideline (i.e., 90 minutes) by 48-108%. This is because once a high-risk patient has been identified in the emergency department, several subsequent manual steps must be taken to get the patient to the catheterization lab, including locating the cardiologist on call, manually calling or paging the cardiologist, waiting for the called cardiologist to arrive, looking at the ECG upon arrival and then making a decision, manually calling the catheterization lab to schedule the procedure, and so forth.

There is a need for a system and a method for providing expedited scheduling of an emergency procedure in the catheterization lab, thereby reducing the time to treatment for a patient newly classified to have a high probability of acute myocardial infarction.

SUMMARY OF THE INVENTION

The present invention is directed to a system and a method for scheduling an emergency procedure in response to detecting that a patient has a high probability of acute myocardial infarction. The system is able to identify patients that are suspected of having acute myocardial infarction (or acute ischemia). This is accomplished based on either data entry at the instrument (ECG cart, defibrillator or patient monitor) or the location of the instrument. The system can be configured such that all ECGs acquired from a certain location (such as a coronary care unit, emergency department or chest pain clinic) can be treated as "suspect acute myocardial infarction". Alternatively, patient symptoms or the reason for testing can be directly entered into the ECG record at the electrocardiograph cart or other instrument. The system uses one or more expert software tools or algorithms to analyze received ECG records.

In accordance with the preferred embodiment, the system comprises a serial comparison program for detecting a new left branch bundle block in a series of ECGs; an ACI-TIPI program for computing a score predictive of acute coronary syndrome; and a 12SL® program which elicits statements associated with acute coronary syndrome based on measurements taken from an ECG. Each of these tools has logic (e.g., thresholds and/or settings) for automatic routing which is configurable by the customer via a graphical user interface. If any sufficient condition for automatic routing is satisfied, the system routes the data (including the underlying ECG record) and an alert to an electronic device which is accessible by the cardiologist "on call". In accordance with the preferred embodiment, the electronic device is a bidirectional pager. Alternatively, the electronic device could be a laptop platform having paging/wireless capability.

In accordance with the preferred embodiment, the alert message comprises a request that the cardiologist consider the need for an emergency treatment or procedure, namely, PTCA, to be performed in a catheterization lab. The cardiologist on call receives the ECG record and decides on an appropriate treatment path. Communicating with the central computer of the MUSES system via the bidirectional pager, the called cardiologist is able to access the previous history of the patient in question. If the cardiologist decides that the requested emergency treatment or procedure should be performed, the cardiologist so advises the MUSE® system. The MUSE® system then accesses the schedules of all accessible catheterization labs across multiple hospitals to identify a lab having optimum time-to-treatment. The MUSE® system also accesses its own database for the records of PTCA procedures performed by each associated catheterization lab. The lab having optimum time-to-treatment is rejected if its records do not exhibit an appropriate volume of PTCA procedures. In accordance with the preferred embodiment, the MUSE® system automatically contacts the selected catheterization lab via a network to schedule the PTCA procedure. The MUSED system also automatically contacts the catheterization lab staff members who are on call via bidirectional pagers. Following receipt of confirmation from the necessary staff and from the catheterization lab, the MUSE® system notifies the relevant medical personnel in charge of the patient of the scheduled procedure and advises them where to route the patient.

Other features and aspects of the invention are described and claimed below.

DETAILED DESCRIPTION OF THE PREFERRED EMBODIMENTS

Figure 1:
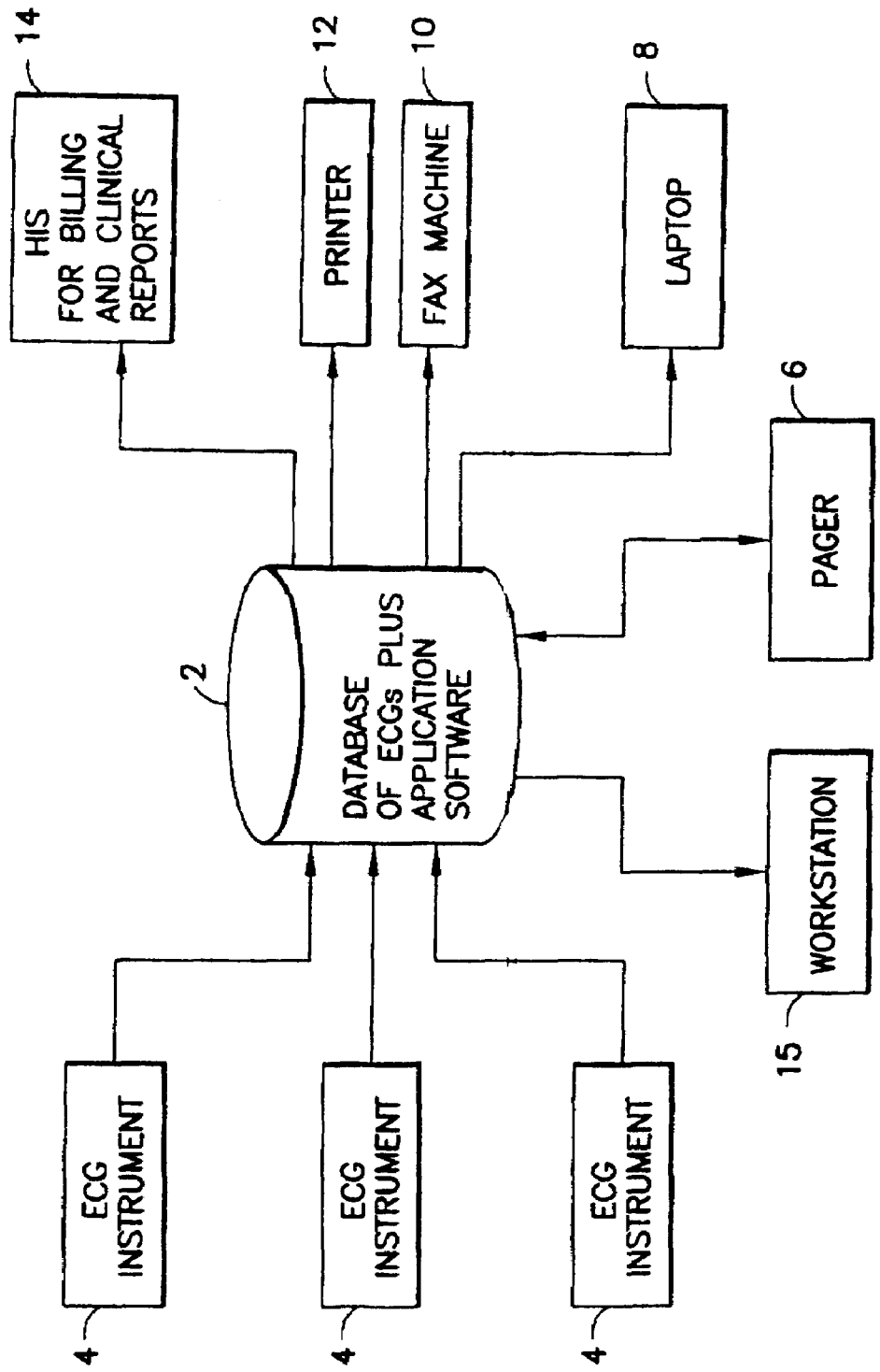
FIG. 1 is a block diagram showing a cardiovascular information system for acquiring, analyzing and routings ECGs.

Referring to FIG. 1, the MUSED ECG management system 2 comprises a database of ECGs and applications software. The software is executed by a conventional server which communicates with a TCP/IP network. The ECGs are stored in a suitable storage medium which is accessible by the server. Any other suitable computer hardware may be used. The MUSE® system 2 receives ECG data from a multiplicity of instruments 4 via a plurality of networks, analyzes that ECG data using various programs such as the serial comparison program, generates reports containing the results of the analysis, and then routes those reports to various systems and peripheral devices. In particular, the MUSE® system has automatic report routing which can send reports to a digital pager 6, a laptop computer 8 (via e-mail), a fax machine 10, a printer 12, a hospital information system 14 for billing and clinical reports, a workstation 15, and other servers on the local area network to which the MUSE® system is connected. The MUSE® system is also programmed to perform automated scheduling of an emergency treatment or procedure in response to receipt of an ECG record which satisfies a user-configurable set of criteria.

Figure 2:
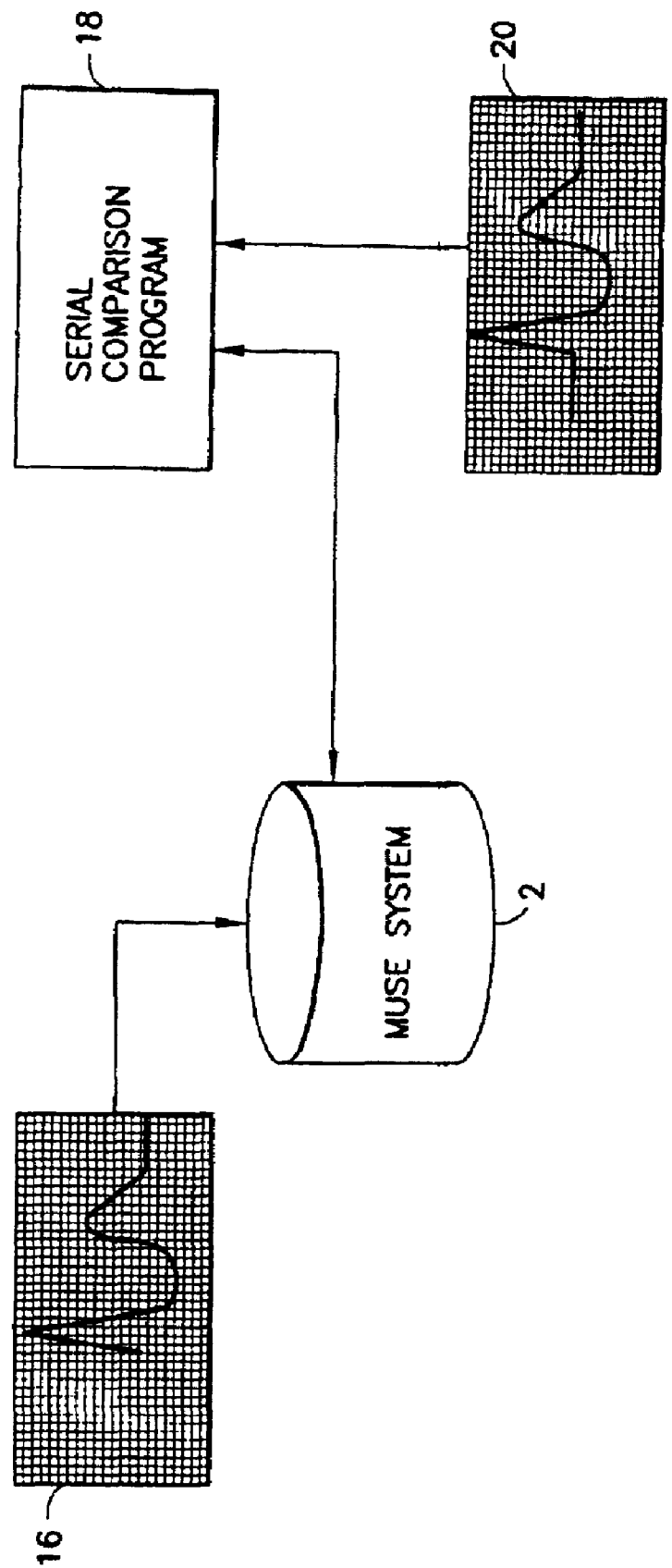
FIG. 2 is a flowchart showing a step performed by a serial comparison program incorporated in the cardiovascular information system shown in FIG. 1.

In accordance with the preferred embodiment of the invention, the applications software of the MUSE® system 2 comprises the previously described serial comparison program 18 (see FIG. 2). The current ECG 16 for a particular patient is acquired by the MUSE® system 2. This newly acquired ECG launches the serial comparison program 18. The serial comparison program 18 retrieves the record for the previous ECG 20 for the particular patient and renders it for comparison with the record for the current ECG for that same patient. The serial program generates an alert when a user-configurable set of criteria are met. The computer of the MUSE® system is programmed to take a particular action in response to generation of the alert.

The applications software of the MUSE® system 2 further comprises the previously described 12SL® program. The 12SL® program generates measurements and diagnostic statements based on analysis of the current ECG. The computer of the MUSE® system is configured to take a particular action in response to generation of a particular diagnostic statement or set of diagnostic statements by the 12SL® program.

The applications software of the MUSE® system 2 further comprises the previously described ACI-TIPI (Acute Cardiac Ischemia Time-Insensitive Predictive Instrument) program, which uses a logistic regression-based equation for computing the probability that the patient is experiencing acute coronary syndrome. The computer of the MUSE® system is configured to take a particular action in response to generation of a probability score above a user-configurable threshold.

In accordance with the preferred embodiment of the invention, the MUSE® system or other central processor is programmed to apply each of the aforementioned expert software tools to each incoming ECG record. Alternatively, any one of the expert software tools can be executed at a location remote from the central computer of the MUSE® system, in which case the results are sent to the MUSE® system via the network or via wireless communication. For example, the 12SL® analysis can be performed by a prehospital defibrillator, the serial comparison can be performed by a satellite computer connected via a local area network to a plurality of bedside monitors (as will be described in detail later), and the ACI-TIPI probability score can be computed by mobile unit comprising an electrocardiograph, a waveform analyzer and a computer programmed to perform the waveform analysis and the functions of the predictive instrument. Upon receipt of an ECG record from any one of these devices, the central computer of the MUSE® is programmed to analyze the reported results and initiate the automated scheduling routine if the results are sufficient to meet any one of the appropriate user-configured criteria or thresholds.

If any one of the three expert software tools produces a result which satisfies the user-configurable criteria for acute myocardial infarction, then the MUSE® system initiates a computer routine for routing the ECG record of interest and an appropriate alert message and/or diagnostic statement to an electronic device which is accessible to the cardiologist "on call". The preferred electronic device is a bidirectional pager 6 (see FIG. 1) or other suitable electronic wireless communication device (e.g., a laptop computer with paging/wireless capability). Preferably the alert message comprises a request that the cardiologist consider the need for an emergency treatment or procedure, namely, PTCA. The cardiologist on call receives the ECG record and decides on an appropriate treatment path. The cardiologist is able to access the previous history of the patient in question. If the cardiologist decides that the requested emergency treatment or procedure should be performed, the cardiologist so advises the MUSE® system. The MUSE® system then accesses the schedules of all accessible catheterization labs across multiple hospitals to identify a lab having optimum time-to-treatment. The MUSE® system also accesses its own database for the records of PTCA procedures performed by each associated catheterization lab. The lab having optimum time-to-treatment is rejected if its records do not exhibit an appropriate volume of PTCA procedures. In accordance with the preferred embodiment, the MUSE® system 2 automatically contacts the selected catheterization lab 66 via the network 78 (shown in FIG. 9) to schedule the PTCA procedure. The MUSED system also automatically contacts the catheterization lab staff members who are on call via bidirectional pagers.

Following receipt of confirmation from the necessary staff and from the catheterization lab, the MUSE® system notifies the relevant medical personnel of the scheduled procedure and advises them where to route the patient. In the case of a coronary care unit, emergency department or chest pain clinic, the relevant medical staff is notified via a network. In the case of an ambulance on its way to the hospital, the emergency medical service is notified via wireless communication. Upon receipt of the notification, the medical staff should immediately undertake whatever steps are needed to prepare the patient for the procedure, such as taking the patient's vital signs, checking for contraindications, establishing an intravenous line, etc.

Figure 3:
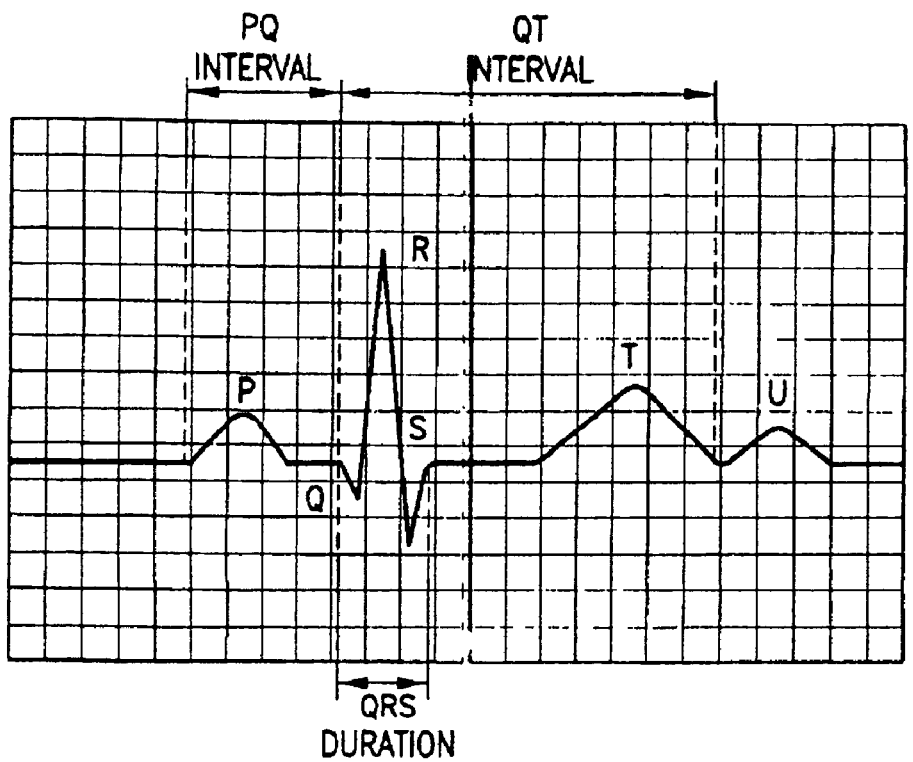
FIGS. 3 and 4 are graphs showing conventional ECG nomenclature.
Figure 4:
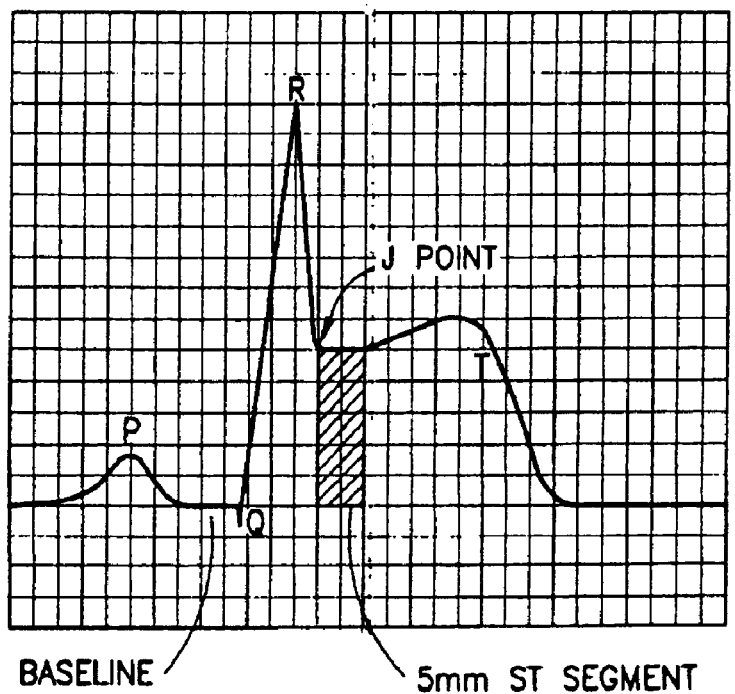
Figure 5:
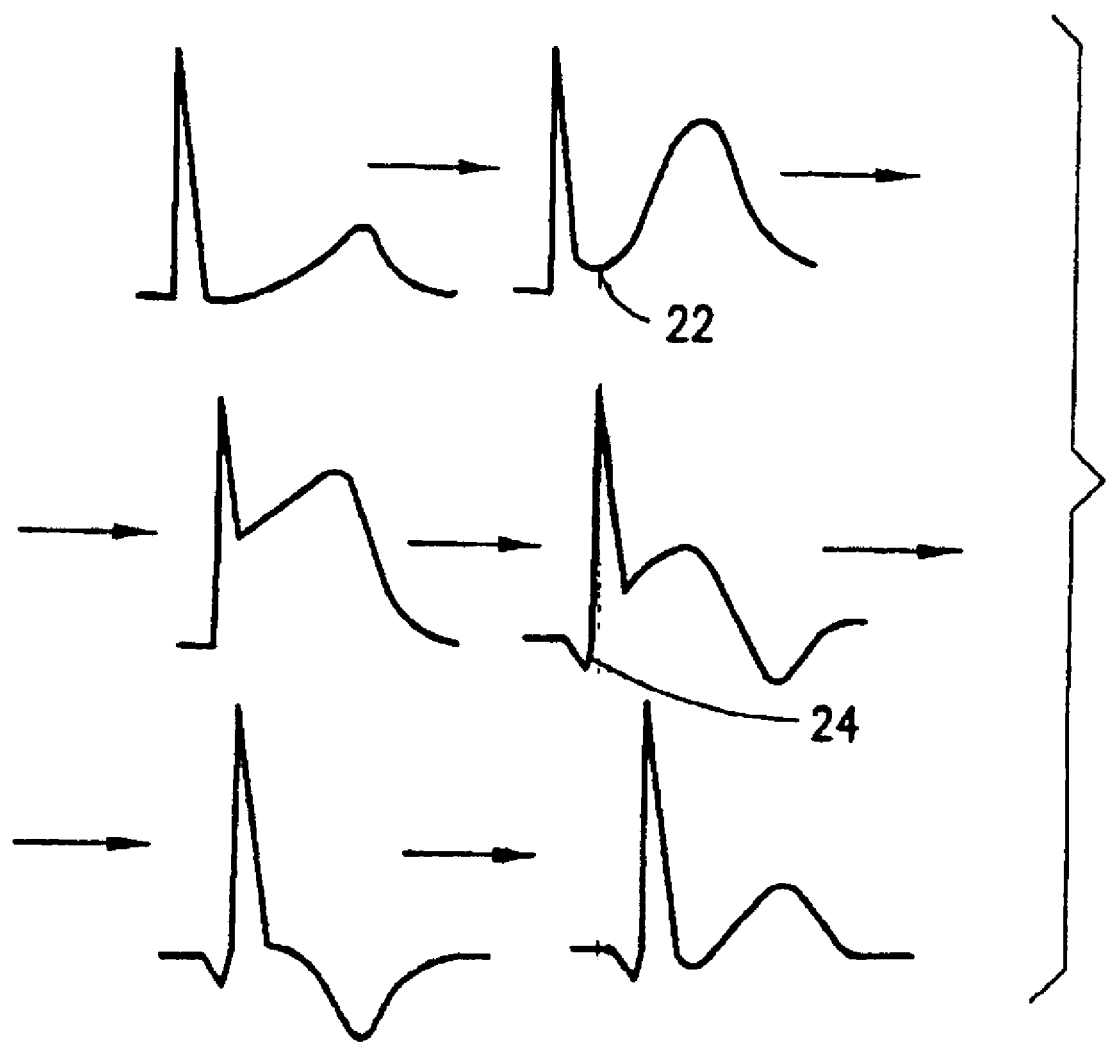
FIG. 5 is a schematic showing a typical sequence of ECG waveforms during evolution of an acute myocardial infarction.

The ECG analysis algorithms used by the MUSE® system will now be described in more detail. The shape of a typical ECG waveform is shown in FIG. 3. The standard nomenclature identifies a P wave, a QRS complex, a T wave, and a U wave. The interval from the onset of the QRS complex to the end of the T wave is referred to as the QT interval. In FIG. 3, the ST segment is shown at the same height as the isoelectric baseline preceding the onset of the QRS complex. In contrast, FIG. 4 shows the ST segment elevated relative to the isoelectric baseline, in this example, by 5 mm. The serial comparison program detects any change in the ST segment elevation, as well as the appearance of a new Q wave. These are not normal variations, but rather are treated as indicative of possible acute myocardial infarction (AMI). The evolution of AMI is depicted in FIG. 5, with a small change in ST segment elevation being indicated by reference numeral 22 and a small new Q wave being indicated by reference numeral 24.

Figure 6:
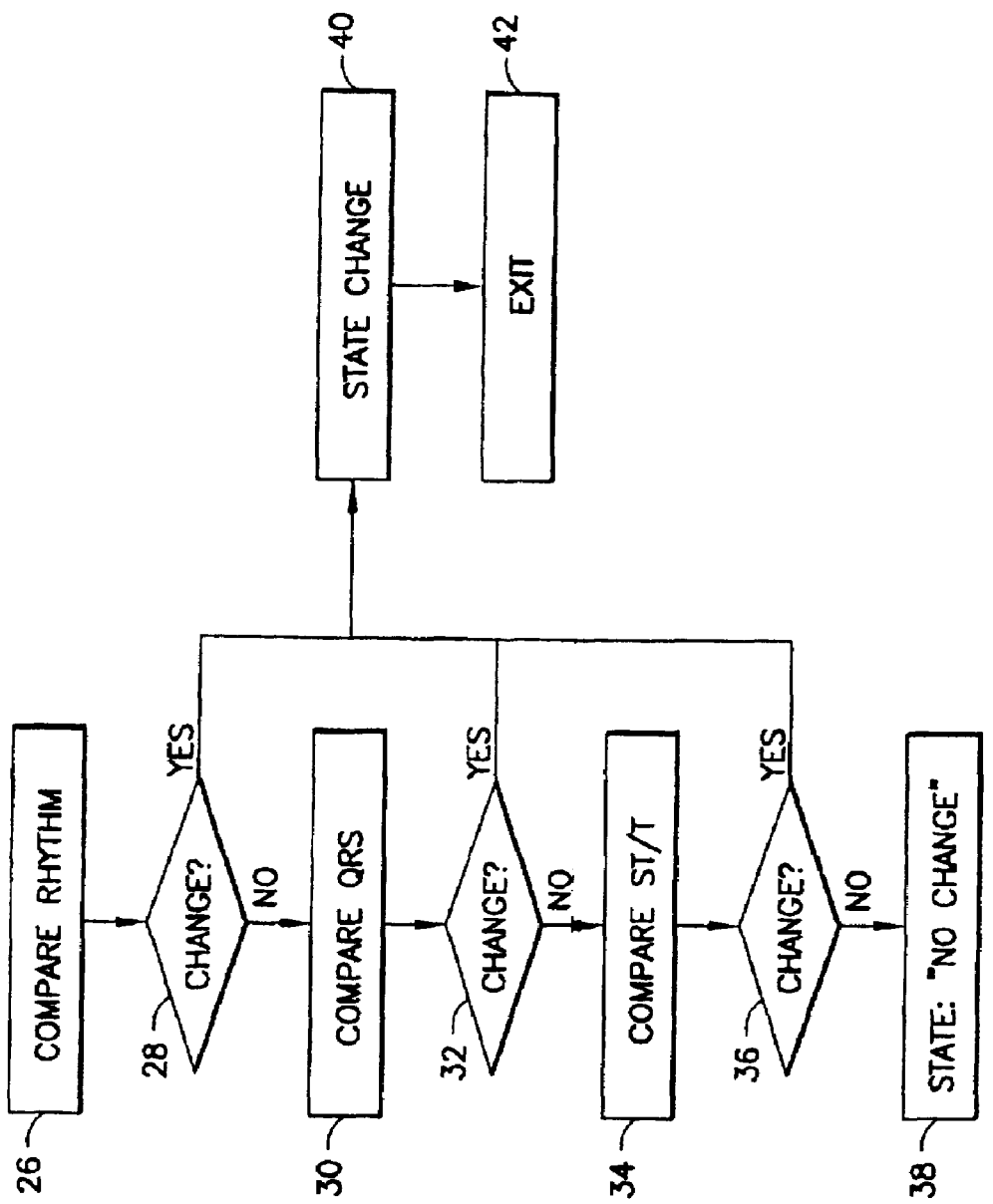
FIG. 6 is a flowchart showing the serial comparison process.

The algorithm performed by the serial comparison program is shown in FIG. 6. In step 26, the dominant rhythms (sinus, ventricular, etc.) are compared using diagnostic statements contained in the current and previous electrocardiogram records. Rhythm modifiers are compared only if the dominant rhythm has not changed. The diagnostic statements are used to detect major changes (step 28) in rhythm that would result in a change in the QRS complex. If a major (i.e., clinically significant) change in rhythm has occurred, the change is stated (step 40) and then the computer exits the serial comparison program (step 42). If no major change in rhythm has occurred, then the QRS complexes for the respective electrocardiograms are compared using statements, measurements and waveform analysis (step 30) for the purpose of detecting conduction and infarction. Changes in the axis and voltage (amplitude) are also detected. Based on the comparison, the serial comparison program determines a change indicative of infarction has occurred (step 32). If "Yes", then the change is stated (step 40). If "No", the standard ST/T analysis using waveforms is performed (step 34). The ST/T analysis looks for the presence/absence of acute myocardial infarction or ischemia. For example, the ST/T analysis looks for an increase in elevation of the ST segment in the waveform for the current electrocardiogram. If the criteria for detection of infarction are met, the change is stated (step 40). If the criteria for detection of infarction are not met, then a statement that no change has occurred is generated in the serial comparison report.

Figure 7:
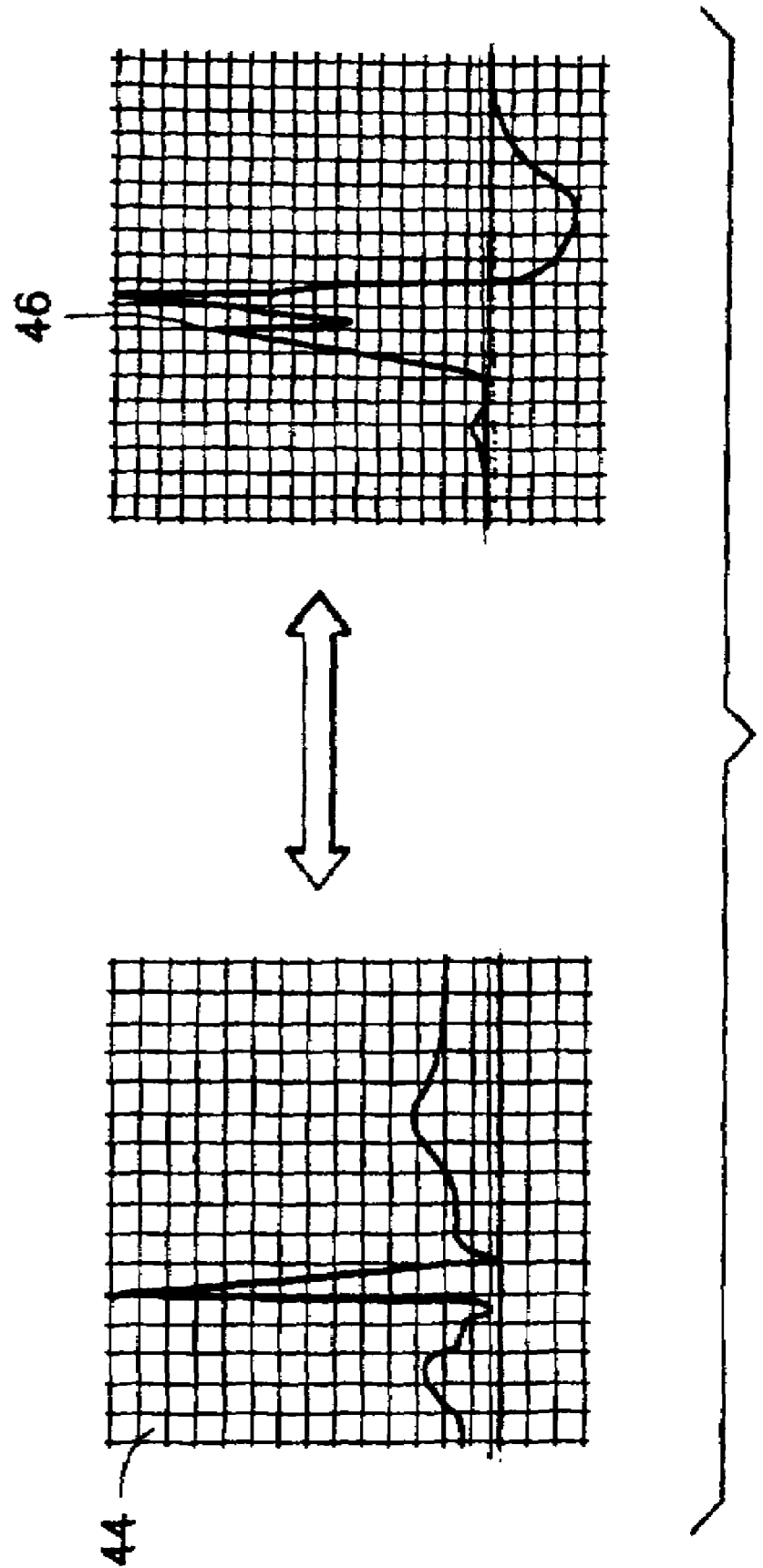
FIG. 7 is a schematic comparing a normal ECG waveform with an LBBB ECG waveform.

An example of a waveform acquired from the V5 lead and having a normal QRS complex is depicted on the left-hand side of FIG. 7. An example of a waveform acquired from the V5 lead and having a QRS complex typical for a left bundle branch block is depicted on the right-hand side of FIG. 7.

In accordance with one preferred embodiment of the invention, the current ECG indicates that a patient is suspected of or has a high probability of acute myocardial infarction. The system can be configured such that all ECGs acquired from a certain location (such as an emergency department chest pain clinic) can be treated as "suspect acute myocardial infarction". Alternatively, patient symptoms or the reason for testing can be directly entered into the ECG record at the electrocardiograph cart. The serial comparison program then senses the "suspect acute myocardial infarction" status of the current ECG record and implements new code within the QRS analysis module.

Figure 8:
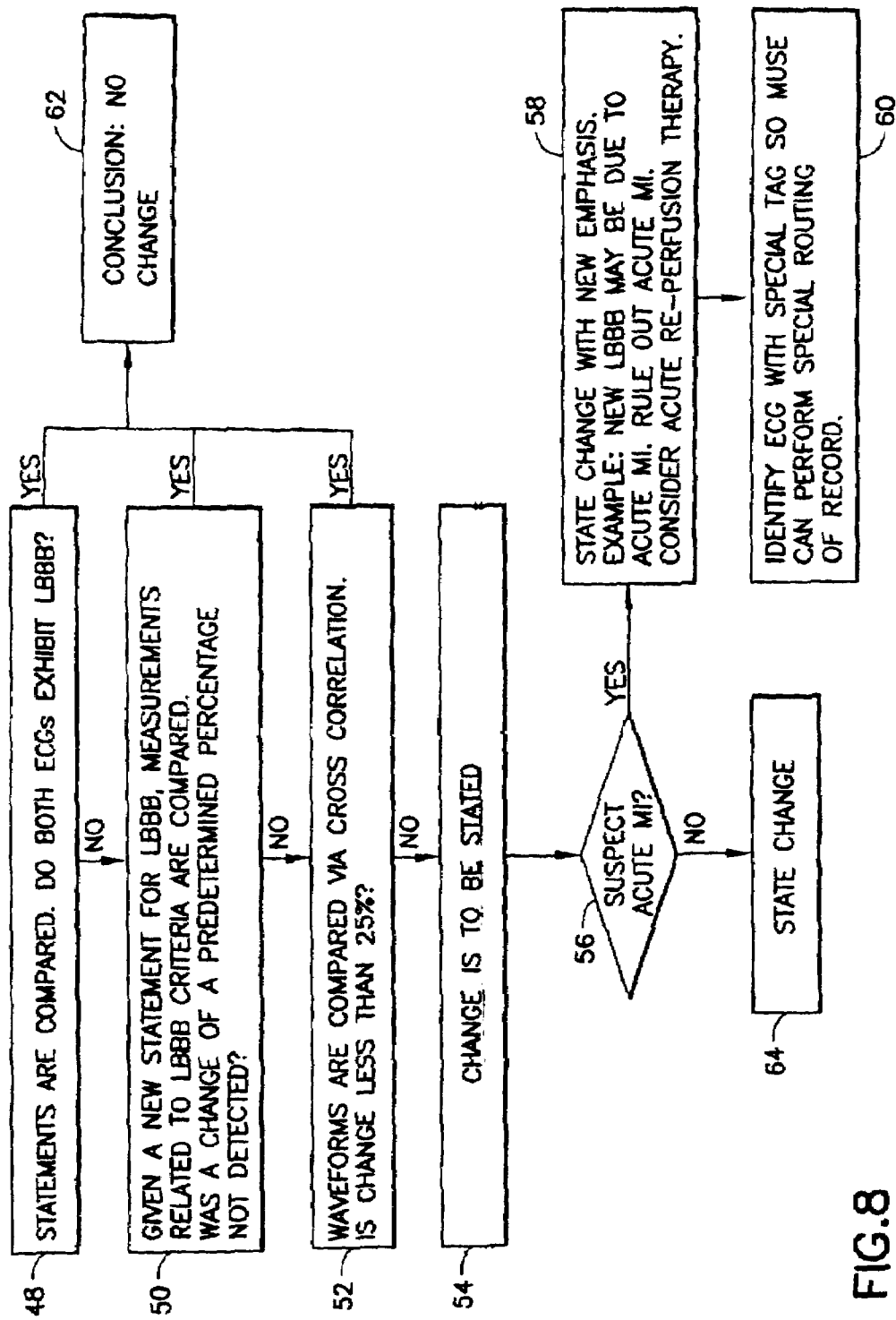
FIG. 8 is a flowchart showing a serial comparison process in accordance with the preferred embodiment of the invention.

The QRS analysis module of the serial comparison program is modified as shown in FIG. 8. In accordance with the preferred embodiments, each current ECG record is compared with a previous ECG record for the same patient (step 48). First, the diagnostic statements for the two ECG records are compared. If both ECGs exhibit LBBB, then no change is stated in the serial comparison report (step 62), i.e., the detected LBBB is not new. However, if only the current ECG record includes a diagnostic statement indicating LBBB, then the algorithm proceeds to the next step. In step 50, measurements related to LBBB criteria are compared. If changes of a predetermined percentage are not present, then no change is stated (step 62). If changes of a predetermined percentage are present, then the algorithm compares the ECG waveforms using cross correlation (step 52). If the change in the current waveform is less than a predetermined percentage, e.g., less than 25%, then no change is stated (step 62). Conversely, if the change in the current ECG waveform, compared to the previous ECG waveform, is greater than 25%, then a determination is made (step 54) that the change will be stated in the serial comparison report.

The system then automatically determines whether the patient belongs to the category comprising patients identified to have a high probability of acute myocardial infarction (step 56). If acute myocardial infarction is not suspected, the system generates a diagnostic statement stating the change (step 64) in the serial comparison report. Alternatively, if acute myocardial infarction is suspected, the system generates a diagnostic statement (step 58) stating that the new left bundle branch block may be due to acute myocardial infarction. The diagnostic statement may further instruct the reader to "Rule out acute MI. Consider acute reperfusion therapy". The current ECG record exhibiting a new LBBB is then identified with a special tag (step 60) and sent to a central database server of the MUSE® system. The MUSE® system then uses this special tag to perform special routing of the current ECG record, e.g., via facsimile or digital pager, to alert on-call medical personnel to the need for immediate treatment, e.g., a PTCA procedure to be performed in a catheterization lab.

As previously mentioned, the applications software of the MUSE® system also comprises the 12SL® program which references a diagnostic statement library based on analysis of ECGs. The diagnostic statement library is used to generate clinical reports, such as an ECG interpretation. The ECG diagnostic statement library on the MUSE® system includes more than a thousand medical diagnostic statements, which are referenced by the 12SL® program. Each medical diagnostic statement is associated with a statement number and an acronym. ECG interpretations or ECG clinical reports may be automatically rendered by the MUSE® system by converting statement numbers that are output by an interpretation program into statement text that is associated with the statement numbers in the diagnostic statement library. Further, customers, such as physicians and hospitals, may add their own diagnostic statements to the diagnostic statement library by referencing a unique statement acronym from the library. After the customer has added their own diagnostic statements, the computer renders a complete text associated with the acronym.

In the above-described diagnostic statement library, a particular clinical finding may be associated with multiple diagnostic statements. For example, acute myocardial infarction (AMI) is associated with more than 20 different statement numbers. To search the database for all patients with AMI, the search mask should contain the logical "OR" of the 20 different diagnostic statements. Further, the person setting up the search would have to know that there were over 20 different diagnostic statements for AMI and would have to know what those diagnostic statements were. If the user were not aware of the 20 different diagnostic statements for AMI, a search with just a single diagnostic statement for AMI would render seemingly reliable results and yet not cull all the pertinent records associated with AMI.

The diagnostic statement library is typically configured as a computer-readable database stored on any of a variety of computer-readable media, such as memory devices, storage devices, hard disk drives, CD ROM drives, optical disk drives, floppy disk drives, tape drives, and the like. Each diagnostic statement in the library comprises a statement number, a statement acronym and statement text. In the MUSE® system, each diagnostic statement in the diagnostic statement library has a statement number which is associated with a corresponding unique statement acronym and corresponding unique statement text. The diagnostic statement library is used and accessed by the physician or technician to generate and edit a clinical report, such as an ECG report.

The 12SL® program can be used to analyze patient ECG data acquired by a patient monitor. The 12SL® program references statement numbers in the diagnostic statement library based on measurements of the ECG waveforms. The 12SL® program may be configured to analyze any of a variety of patient data and then export a plurality of statement numbers to a report generator. The report generator communicates with the diagnostic statement library and converts the statement numbers into text strings by accessing the diagnostic statement corresponding to each statement number to elicit the corresponding statement text. In this manner, the report generator can generate a report comprising text string statements. This clinical report is then stored, and may be searched, retrieved and read by physicians, technicians and/or other users.

In accordance with an enhanced diagnostic statement library available on the MUSE® system, each diagnostic statement further comprises a diagnostic classifier. In particular, the diagnostic classifier may comprise a predictor of perioperative cardiovascular risk, e.g., "Minor Risk" or "Major Risk". Preferably, these diagnostic classifications are configurable by the user to provide customized classifications and/or instructions. For example, a set of diagnostic statements may be classified by including in each statement of the set a diagnostic classifier which indicates association with a particular clinical diagnosis, such as acute myocardial infarction. Also, a diagnostic classifier could identify a particular emergency treatment or procedure, such as percutaneous transluminal coronary angioplasty (PTCA), which should be considered. In this example, the relevant diagnostic classifier might be "PTCA Alert" or "PTCA Candidate". Alternatively, the system could be configured to take emergency action in response to any ECG record comprising at least a threshold number of statement numbers representing statements belonging to a particular diagnostic classification. Automatic routing would be performed by the MUSE® system in response to detection of that threshold number.

The MUSE® system can be configured by the user such that automatic routing and scheduling occurs in response to a probability P equal to at least a predetermined threshold.

Figure 9:
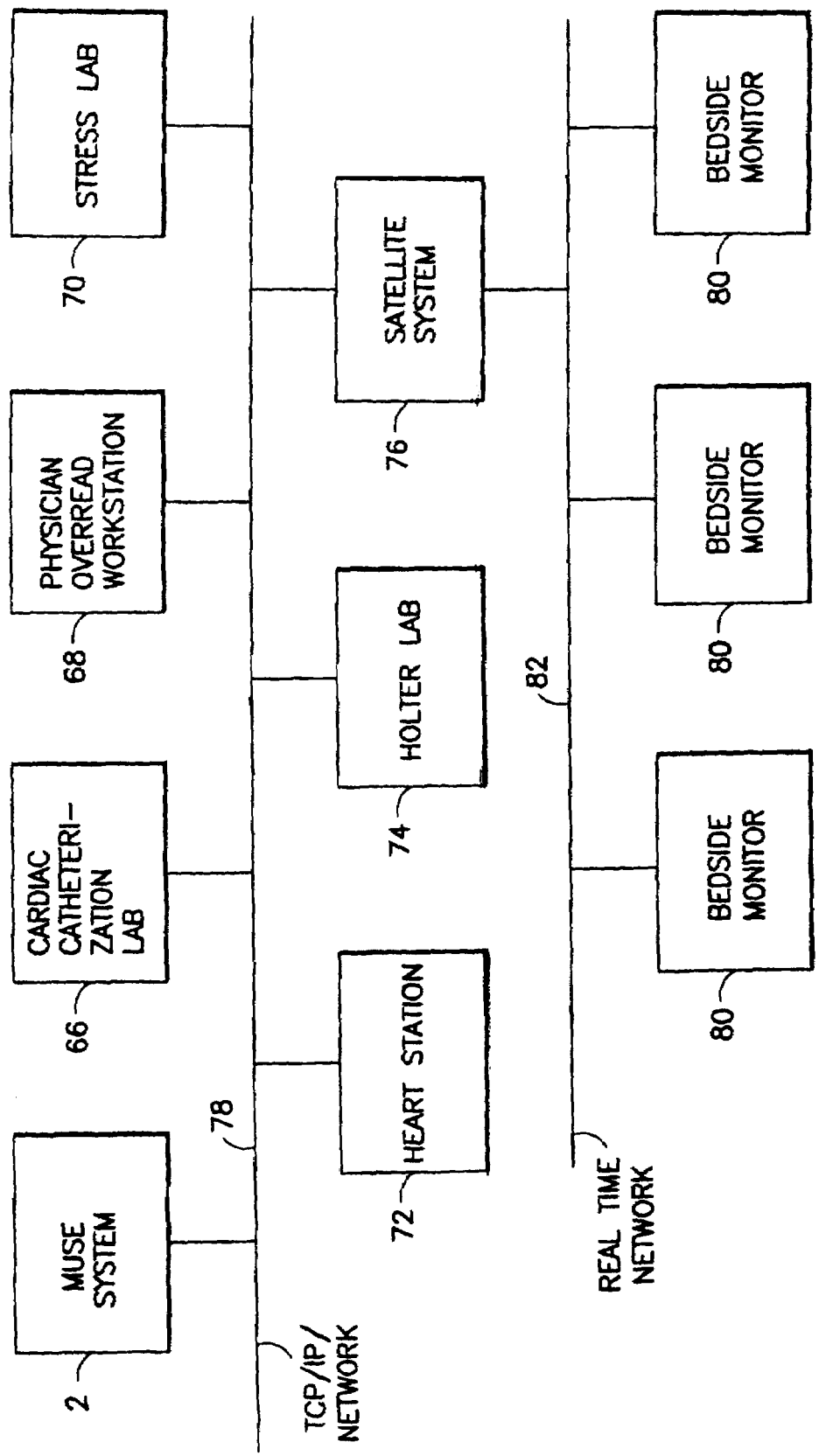
FIG. 9 is a block diagram showing a cardiovascular information network having a satellite system for detecting changes in ECGs acquired by bedside patient monitors in accordance with one preferred embodiment of the invention.

FIG. 9 generally depicts one possible configuration for an integrated system installed in a hospital or other health care facility. The MUSE® ECG management system 2 communicates with other departments and stations in the hospital via a TCP/IP network 78. For the purpose of illustration, FIG. 9 shows a cardiac catheterization lab 66, a physician overread workstation 68, a stress lab 70, a heart station 72, and a Holter lab 74, all of which are well known in the art. It is also known in the art to provide a satellite system 76 which communicates with the MUSE® system 2 via the TCP/IP network 78. The satellite system 76 typically comprises a computer programmed to receive and analyze ECG records transmitted from a plurality of bedside monitors 80 via a real-time local area network 82. The bedside monitors 80 continuously monitor patients. The patients are typically located in a coronary care unit, emergency department or chest pain clinic. The satellite system 76 acquires 12-lead ECGs every minute from the monitors and trends the results. If measurements change above a predetermined threshold, an alert is generated. The acquired ECG records are sent by the satellite system 76 to the MUSE® system via the network 78. The MUSE® system also receives a final report of trends from the satellite system. The MUSE® system generates reports and sends those reports to other devices and systems. Conventional routing software uses several identifiers for routing reports, such as location, report status, and normal/abnormal.

In accordance with one preferred embodiment of the invention, the computer of the satellite system 76 is programmed to perform serial analysis on the ECG records continuously acquired from the bedside monitors 80. The previous ECG records for monitored patients are retrieved from the central ECG database of the MUSE® system 2.

In accordance with one preferred embodiment, the computer of the satellite system is programmed to request and receive a previous electrocardiogram record for each patient from the central database; receive the current electrocardiogram record for each patient from a respective bedside monitors; and determine whether a new left bundle branch block is present in each patient based on a comparison of data in the current and previous electrocardiogram records. The details of the determining step are shown in FIG. 8 and will not be described again. If it is determined that a new LBBB is present for any patient, the computer generates a diagnostic statement or an alert indicating that that the new left bundle branch block may be due to acute myocardial infarction. In response to the alert, expedited treatment for acute myocardial infarction is provided.

In accordance with a further aspect of the invention, a specific routing tag is added to the current ECG record based on the automated diagnosis of a new LBBB. The satellite system 76 then sends the current ECG record to the MUSE® system via the network 78. The special routing tag in the transmitted current ECG record enables the MUSE® system to automatically perform special routing of the current ECG record and an appropriate alert message, e.g., to a cardiologist on call. In response to the called cardiologist's decision to proceed with the emergency treatment, the MUSE® system automatically selects the optimum catheterization lab and automatically schedules the selected lab and the on-call staff associated with that lab.

While the invention has been described with reference to preferred embodiments, it will be understood by those skilled in the art that various changes may be made and equivalents may be substituted for elements thereof without departing from the scope of the invention. In addition, many modifications may be made to adapt a particular situation to the teachings of the invention without departing from the essential scope thereof. Therefore it is intended that the invention not be limited to the particular embodiment disclosed as the best mode contemplated for carrying out this invention, but that the invention will include all embodiments falling within the scope of the appended claims.

As used in the claims, the terms "current" and "previous" are used to refer to electrocardiogram records which were acquired at different times, the "current" electrocardiogram record being acquired at a time subsequent to the time when the "previous" electrocardiogram record was acquired.

The invention claimed is:

1. A method for scheduling an emergency procedure, comprising the steps of:
    acquiring an electrocardiogram record for a particular patient, said electrocardiogram record comprising simultaneously acquired 12-1lead electrocardiograms;
    sending said electrocardiogram record to a computer;
    said computer determining that said particular patient has a high probability of acute coronary syndrome based at least partly on an automated analysis of data in said electrocardiogram record;
    said computer automatically routing a communication to an electronic device accessible to a cardiologist on call in response to said determination by said computer that said particular patient has a high probability of acute coronary syndrome, said communication comprising said electrocardiogram record and results of said automated analysis;
    after said routing of said communication to said electronic device, said computer receiving a message from said cardiologist having content indicating that said patient should undergo an emergency procedure for treatment of acute coronary syndrome; and
    in response to said message from the cardiologist, said computer automatically scheduling said emergency procedure at an emergency coronary treatment facility.

2. The method as recited in claim 1, wherein said emergency coronary treatment facility is a catheterization lab.

3. The method as recited in claim 1, wherein said emergency procedure is percutaneous transluminal coronary angioplasty.

4. The method as recited in claim 1, wherein said automatic routing step is performed via a wireless communication channel.

5. The method as recited in claim 1, wherein said automatic scheduling step is performed via a network.

6. The method as recited in claim 1, wherein said automatic scheduling step comprises the steps of accessing a respective schedule for each of a plurality of emergency coronary treatment facilities and selecting an emergency coronary treatment facility having an optimum time-to-treatment.

7. The method as recited in claim 1, wherein said automatic scheduling step comprises the steps of accessing a respective schedule for each of a plurality of emergency coronary treatment facilities and selecting an emergency coronary treatment facility which has performed a number of said emergency procedures greater than a predetermined threshold number.

8. The method as recited in claim 1, wherein said automated analysis comprises performing a serial comparison of current and previous electrocardiogram records of said particular patient to determine whether a new left bundle branch block is present.

9. The method as recited in claim 1, wherein said automated analysis comprises the steps of:
    generating diagnostic statements as a function of data in an electrocardiogram record of said particular patient; and
    determining whether the number of generated diagnostic statements belonging to a predetermined diagnostic classification equals at least a predetermined threshold number.

10. The method as recited in claim 9, wherein said diagnostic classification identifies diagnostic statements associated with acute coronary syndrome.

11. The method as recited in claim 1, wherein said automatic scheduling step comprises the step of automatically notifying staff members on call at said emergency coronary treatment facility regarding the scheduled procedure.

12. A system for scheduling an emergency procedure, comprising:
    an instrument for acquiring an electrocardiogram record for a particular patient, said electrocardiogram record comprising simultaneously acquired 12-lead electrocardiograms;
    an electronic device accessible to a cardiologist on call;
    a computer located at a site different than the sites where said instrument and said electronic device are located;
    means for sending said electrocardiogram record from said instrument to said computer via a network; and
    an emergency coronary treatment facility,
    wherein said computer is programmed to perform the following steps:
        determining that said particular patient has a high probability of acute coronary syndrome based at least partly on an automated analysis of data in said electrocardiogram record;
        routing a communication to said electronic device in response to said determination by said computer that said particular patient has a high probability of acute coronary syndrome, said communication comprising said electrocardiogram record and results of said automated analysis;
        after said routing of said communication to said electronic device, said computer receiving a message from said cardiologist having content indicating that said patient should undergo an emergency procedure for treatment of acute coronary syndrome; and
        scheduling said emergency procedure at said emergency coronary treatment facility in response to said message from said cardiologist.

13. The system as recited in claim 12, wherein said emergency coronary treatment facility is a catheterization lab.

14. The system as recited in claim 12, wherein said emergency procedure is percutaneous transluminal coronary angioplasty.

15. The system as recited in claim 12, wherein said computer is further programmed to notify staff members on call at said emergency coronary treatment facility regarding the scheduled procedure.

16. The system as recited in claim 12, further comprising an electronic bidirectional wireless communication device accessible to the cardiologist.

17. The system as recited in claim 12, wherein said instrument, said computer and said emergency coronary treatment facility communicate via a network.

18. The system as recited in claim 12, wherein said computer is further programmed to access a respective schedule for each of a plurality of emergency coronary treatment facilities and select an emergency coronary treatment facility having a schedule which provides an optimum time-to-treatment.

19. The system as recited in claim 12, further comprising a storage medium for storing records of emergency procedures performed by emergency coronary treatment facilities, wherein said computer is further programmed to access said records of emergency procedures and to reject an emergency coronary treatment facility which has not performed a number of said emergency procedures greater than a predetermined threshold number.

20. The system as recited in claim 12, wherein said computer is further programmed to set thresholds for use in said automated analysis in accordance with configuration instructions input via a graphical user interface.

21. The system as recited in claim 12, wherein said computer is programmed to perform a serial comparison of current and previous electrocardiogram records of said particular patient to determine whether a new left bundle branch block is present.

22. The system as recited in claim 12, wherein said computer is programmed to perform the steps of:
   generating diagnostic statements as a function of data in an electrocardiogram record of said particular patient; and
   determining whether the number of generated diagnostic statements belonging to a predetermined diagnostic classification equals at least a predetermined threshold number.

23. The system as recited in claim 22, wherein said diagnostic classification identifies diagnostic statements associated with acute coronary syndrome.

* * * * *